(12) United States Patent
Shuros et al.

(10) Patent No.: US 11,446,505 B2
(45) Date of Patent: Sep. 20, 2022

(54) HIS-BUNDLE PACING FOR ATRIOVENTRICULAR BLOCK

(71) Applicant: Cardiac Pacemakers, Inc., St. Paul, MN (US)

(72) Inventors: Allan Charles Shuros, St. Paul, MN (US); David Arthur Casavant, Reading, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 47 days.

(21) Appl. No.: 16/886,531

(22) Filed: May 28, 2020

(65) Prior Publication Data
US 2020/0376280 A1    Dec. 3, 2020

Related U.S. Application Data

(60) Provisional application No. 62/855,396, filed on May 31, 2019.

(51) Int. Cl.
*A61N 1/365*    (2006.01)

(52) U.S. Cl.
CPC ..... *A61N 1/36585* (2013.01); *A61N 1/36542* (2013.01); *A61N 1/36592* (2013.01)

(58) Field of Classification Search
None
See application file for complete search history.

(56) References Cited

U.S. PATENT DOCUMENTS

| | | |
|---|---|---|
| 6,609,027 B2 | 8/2003 | Kroll et al. |
| 6,772,005 B2 | 8/2004 | Casavant et al. |
| 8,180,449 B2 | 5/2012 | Dewals |
| 8,588,907 B2 | 11/2013 | Arcot-Krishnamurthy et al. |
| 2010/0076063 A1* | 3/2010 | Sharma ............... C07K 14/705 514/44 R |

(Continued)

OTHER PUBLICATIONS

Contractor, Tahmeed, et al., "Cardiac resynchronization therapy for rate-related bundle branch block: Is there a role for His-bundle pacing?", Heart Rhythm Case Reports, vol. 4, No. 10, Oct. 2018, 475-479.

(Continued)

*Primary Examiner* — Brian T Gedeon
(74) *Attorney, Agent, or Firm* — Schwegman Lundberg & Woessner, P.A.

(57) ABSTRACT

Systems and methods for dynamically controlling His-bundle pacing (HBP) according to an indication of a rate-related or intermittent atrioventricular (AV) block in a subject are disclosed. An exemplary medical system includes an AV conduction monitor to detect an indication of either a presence or an absence of intermittent or rate-related AV conduction disturbance using physiologic information of the subject. In the event that an intermittent or rate-related AV conduction disturbance is present, a control circuit provides a control signal to an electrostimulation circuit to deliver HBP pulses. If there is no indication of intermittent or rate-related AV conduction disturbance, or a previously detected intermittent or rate-related AV conduction disturbance has been terminated, the control circuit withholds or discontinues delivery of the HBP pulses to promote intrinsic ventricular conduction and activation.

20 Claims, 7 Drawing Sheets

(56) References Cited

U.S. PATENT DOCUMENTS

2010/0298901 A1* 11/2010 Sommer .............. A61B 5/349
  607/14
2018/0085021 A1* 3/2018 Chakravarthy ...... A61B 5/0022

OTHER PUBLICATIONS

Sen, Naresh, et al., "The rate dependent bundle branch block and mechanical dyssynchrony leads heart failure and beneficial effect of Cardiac Resynchronization Therapy", J Clin Exp Cardiolog 2015, 6:10, p. 76.

Vasheghani-Farahani, Ali, et al., "Reversible left bundle branch block should be mentioned in cardiac", ARYA Atheroscler Apr. 15, 2016; vol. 12; Issue 3, 153-155.

* cited by examiner

HIS-BUNDLE PACING FOR ATRIOVENTRICULAR BLOCK

CLAIM OF PRIORITY

This application claims the benefit of priority under 35 U.S.C. § 119(e) of U.S. Provisional Patent Application Ser. No. 62/855,396, filed on May 31, 2019, which is herein incorporated by reference in its entirety.

TECHNICAL FIELD

This document relates generally to medical systems, and more particularly, to systems, devices and methods for pacing of cardiac conductive tissue, such as a His bundle or a bundle branch.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways known as His-Purkinje system to various regions of the heart to excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction and/or deteriorated myocardium may cause dyssynchronous contraction of the heart, resulting in poor hemodynamic performance, including a diminished blood supply to the heart and the rest of the body. For example, an abnormal delay in the transmission of the action potentials in the His bundle may cause irregular or dyssynchronous contractions of the ventricles.

Artificial cardiac pacing system have been used to rectify cardiac dyssynchrony and to improve hemodynamic performance. The artificial cardiac pacing system may provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apical pacing directly excites the ventricular myocardium in an unnatural way involving slow muscle-muscle contraction. Normally, ventricular excitation involves rapid coordinate activation via action potentials that are propagated through the natural conduction pathways. Studies have shown that, in some patients, the cardiac dyssynchrony induced by RV apical pacing, partially due to the interventricular delay in impulse propagation to the left ventricle, can result in adverse ventricular changes including enlarged ventricles and heart failure when delivered over the long term. Moreover, permanent changes in myocardial perfusion and structure may develop over time in these patients, which may further decrease cardiac output and deteriorate ventricular function. BiV pacing involves RV pacing via one lead, and LV pacing via another lead, and has been demonstrated to restore synchronized contraction of both ventricles. However, the potential adverse impact on ventricular function produced by the RV apical pacing may still exist in BiV pacing. Muscle-muscle activation via epicardial LV pacing is also known to result in a less vigorous contraction.

Some studies have shown that blockage in left bundle branch block is most often located at the root of the left bundle at the His bundle junction, or in the His bundle itself. Pacing the distal His bundle region located within the atrioventricular (or interventricular) junction has shown to result in electrical "reconnection" of the left bundle and restored left ventricular activation.

OVERVIEW

This document discusses systems, devices, and methods for controlling His-bundle pacing (HBP) according to an indication of a rate-related or intermittent atrioventricular (AV) block in a subject. An exemplary medical system includes AV conduction monitor configured to detect an indication of presence or absence of intermittent or rate-related AV conduction disturbance using physiologic information of a subject. In the event that an intermittent or rate-related AV conduction disturbance is present, a control circuit may provide a control signal to an electrostimulation circuit to deliver HBP pulses. If there is no indication of intermittent or rate-related AV conduction disturbance, or a previously detected intermittent or rate-related AV conduction disturbance has been terminated, the control circuit may withhold or discontinue delivery of the HBP pulses to promote intrinsic ventricular conduction and activation.

Example 1 is a medical-device system comprising: an atrioventricular (AV) conduction monitor configured to detect an indication of either a presence or an absence of an intermittent or rate-related AV conduction disturbance in a heart of a subject using physiologic information of the subject; and a pacing control circuit configured to control an electrostimulation circuit to generate His-bundle pacing (HBP) pulses, and to provide a control signal to: deliver HBP pulses to stimulate a physiologic conduction pathway of the heart in response to a detected indication of a presence of intermittent or rate-related AV conduction disturbance; and withhold or discontinue delivery of the HBP pulses in response to a detected indication of an absence of intermittent or rate-related AV conduction disturbance.

In Example 2, the subject matter of Example 1 optionally includes the AV conduction monitor that can be configured to: detect a heart rate (HR) of the subject; and detect an indication of a presence of intermittent or rate-related AV conduction disturbance in response to the HR exceeding a HR threshold, or an indication of an absence of intermittent or rate-related AV conduction disturbance in response to the HR is below the HR threshold.

In Example 3, the HR of Example 2 optionally includes a sensed atrial heart rate.

In Example 4, the HR of Example 3 optionally includes an atrial pacing rate driven by a physiologic sensor.

In Example 5, the subject matter of Example 4 optionally includes the physiologic sensor that can include an activity sensor or a respiration sensor, and the AV conduction monitor can be configured to determine a sensor-drive atrial pacing rate using sensor measurements from the activity sensor or the respiration sensor.

In Example 6, the subject matter of claim 2 optionally includes the HR that can include a far-field atrial heart rate sensed outside an atrium of the heart.

In Example 7, the subject matter of any one or more of Examples 2-6 optionally includes the AV conduction monitor that can be configured to monitor HR continuously or periodically during the delivery of the HBP pulses, and the pacing control circuit that can be configured to provide a control signal to: continue delivery of the HBP pulses in response to an indication of a presence of intermittent or rate-related AV conduction disturbance; and discontinue delivery of the HBP pulses in response to an indication of an absence of intermittent or rate-related AV conduction disturbance.

In Example 8, the subject matter of any one or more of Examples 1-7 optionally includes the AV conduction monitor that can be configured to: determine a QRS width metric; and detect an indication of a presence of intermittent AV conduction disturbance in response to the QRS width metric exceeding a QRS width threshold, or an indication of an absence of intermittent AV conduction disturbance in response to the QRS width metric falling below the QRS width threshold.

In Example 9, the subject matter of any one or more of Examples 1-8 optionally includes the physiologic information can include cardiac acceleration information indicative of heart sounds (HS).

In Example 10, the subject matter of Example 9 optionally includes the cardiac acceleration information that can include an S1 heart sound intensity metric, and the AV conduction monitor can be configured to detect an indication of a presence of intermittent AV conduction disturbance in response to the S1 heart sound intensity metric falling below an S1 intensity threshold, or an indication of an absence of intermittent AV conduction disturbance in response to the S1 heart sound intensity metric exceeding the S1 intensity threshold.

In Example 11, the subject matter of any one or more of Examples 1-10 optionally includes the physiologic information can include a cardiac timing information.

In Example 12, the subject matter of Example 11 optionally includes the cardiac timing information that can include a pre-ejection period (PEP), and the AV conduction monitor can be configured to detect an indication of a presence of intermittent AV conduction disturbance in response to the PEP exceeding a PEP threshold, or an indication of an absence of intermittent AV conduction disturbance in response to the S1 intensity metric falling below the PEP threshold.

In Example 13, the subject matter of any one or more of Examples 1-12 optionally includes the AV conduction monitor that can be configured to monitor heart rate (HR) and a physiologic parameter different from HR; and the pacing control circuit can be configured to, in response to the monitored HR exceeding a HR threshold, trigger the AV conduction monitor to detect an indication of presence or absence of intermittent or rate-dependent AV conduction disturbance using the physiologic parameter.

In Example 14, the subject matter of any one or more of Examples 1-13 optionally includes the AV conduction monitor that can be configured to: monitor heart rate (HR) and a physiologic parameter different from HR; detect the indication of either a presence or an absence of an intermittent or rate-related AV conduction disturbance using the physiologic parameter; and detect a HR corresponding to the detected indication of presence of intermittent or rate-related AV conduction disturbance. The pacing control circuit can be configured to provide a control signal to deliver, or withhold or discontinue, the HBP pulses using the detected HR corresponding to the detected indication of presence of intermittent or rate-related AV conduction disturbance.

In Example 15, the subject matter of Example 14 optionally includes an output circuit configured to display the detected HR corresponding to the detected intermittent or rate-related AV conduction disturbance.

Example 16 is a method for pacing a physiologic conduction pathway including a His bundle or a bundle branch of the heart. The method comprises, via a medical-device system, steps of: detecting an indication of either a presence or an absence of an intermittent or rate-related AV conduction disturbance in a heart of a subject using physiologic information of the subject; and in response to an indication of a presence of intermittent or rate-related AV conduction disturbance, delivering HBP pulses to stimulate a physiologic conduction pathway; and in response to an indication of an absence of intermittent or rate-related AV conduction disturbance, withholding or discontinuing delivery of the HBP pulses.

In Example 17, the subject matter of Example 16 optionally includes detecting an indication of either a presence or an absence of an intermittent or rate-related AV conduction disturbance that can include steps of: detecting a heart rate (HR) of the subject; and detecting an indication of a presence of intermittent or rate-related AV conduction disturbance in response to the HR exceeding a HR threshold, or an indication of an absence of intermittent or rate-related AV conduction disturbance in response to the HR is below the HR threshold.

In Example 18, the subject matter of any one or more of Examples 16-17 optionally includes detecting an indication of either a presence or an absence of an intermittent or rate-related AV conduction disturbance that can include steps of: determining a QRS width metric; and detecting an indication of a presence of intermittent AV conduction disturbance in response to the QRS width metric exceeding a QRS width threshold, or an indication of an absence of intermittent AV conduction disturbance in response to the QRS width metric falling below the QRS width threshold.

In Example 19, the subject matter of any one or more of Examples 16-18 optionally includes detecting an indication of either a presence or an absence of an intermittent or rate-related AV conduction disturbance that can include steps of: determining an S1 heart sound intensity metric; and detecting an indication of a presence of intermittent AV conduction disturbance in response to the S1 heart sound intensity metric falling below an S1 intensity threshold, or an indication of an absence of intermittent AV conduction disturbance in response to the S1 heart sound intensity metric exceeding the S1 intensity threshold.

In Example 20, the subject matter of any one or more of Examples 16-19 optionally includes detecting an indication of either a presence or an absence of an intermittent or rate-related AV conduction disturbance that can include steps of: determining a pre-ejection period (PEP); and detecting an indication of a presence of intermittent AV conduction disturbance in response to the PEP exceeding a PEP threshold, or an indication of an absence of intermittent AV conduction disturbance in response to the S1 intensity metric falling below the PEP threshold.

In Example 21, the subject matter of any one or more of Examples 16-20 optionally includes steps of: monitoring heart rate (HR) and a physiologic parameter different from HR; and in response to the monitored HR exceeding a HR threshold, triggering the detection of an indication of presence or absence of intermittent or rate-dependent AV conduction disturbance using the physiologic parameter.

In Example 22, the subject matter of any one or more of Examples 16-21 optionally includes steps of: monitoring heart rate (HR) and a physiologic parameter different from HR; detecting the indication of either a presence or an absence of an intermittent or rate-related AV conduction disturbance using the physiologic parameter; detecting a HR corresponding to the detected indication of presence of intermittent or rate-related AV conduction disturbance; and providing a control signal to deliver, or withhold or discontinue, the HBP pulses using the detected HR corresponding to the detected indication of presence of intermittent or rate-related AV conduction disturbance.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
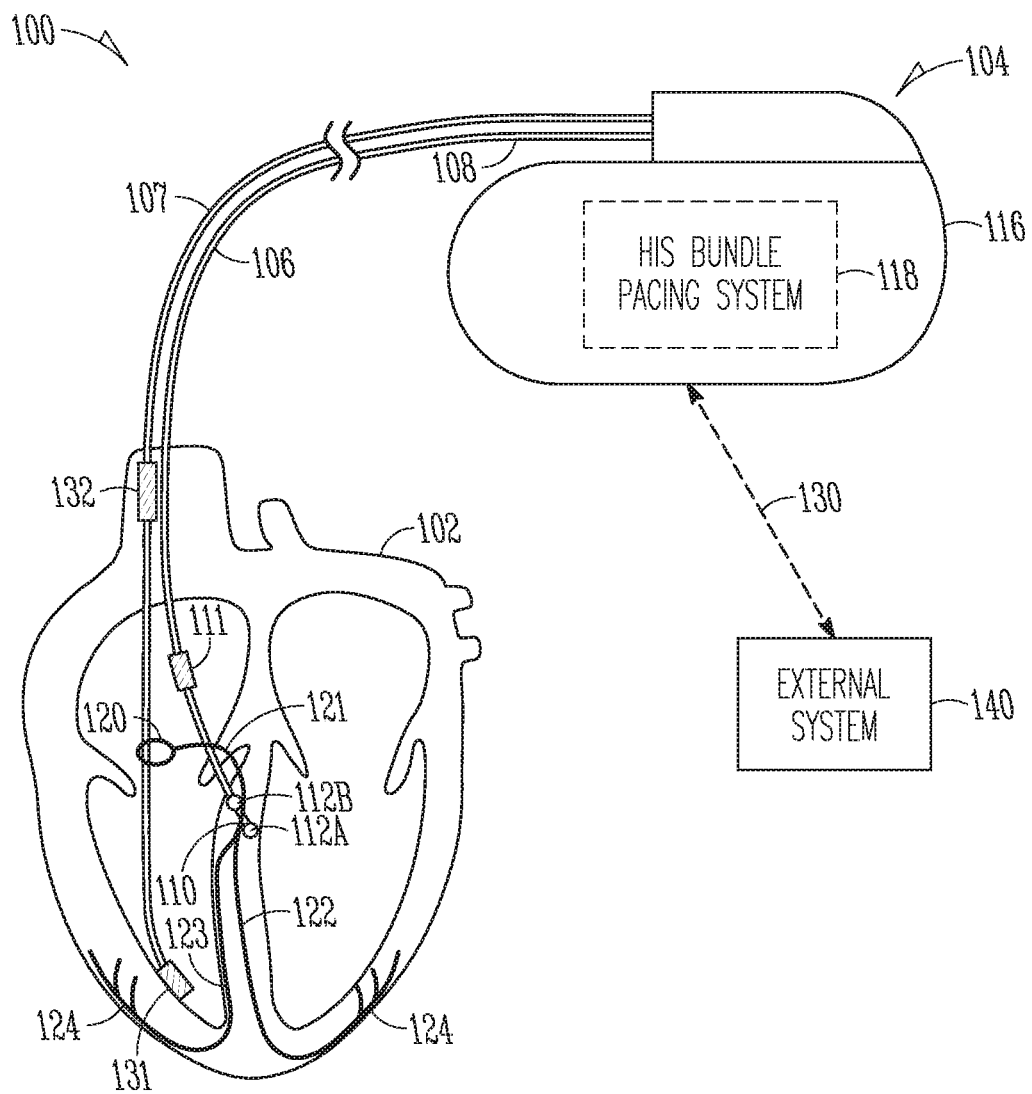
FIG. 1 illustrates generally an example of a cardiac disease management system and portions of an environment in which the system may operate.

Hemodynamic response to artificial pacing may depend on many factors, including pacing site selection and pacing configurations. Many patients receiving artificial pacing therapy have an intact His bundle and the natural cardiac electrical conduction system in the ventricles, and therefore having normal ventricular activation. Conventional cardiac pacing such as long-term RV apical pacing (i.e., pacing at RV apex) may cause a decrease in cardiac output and efficiency due to the uncoordinated contraction sequence. This dyssynchrony may eventually cause adverse long-term effects. Dyssynchronous contraction of the ventricles occurs during conventional RV pacing because the activation sequence may be much slower and propagate slowly from the right to the left ventricle across the interventricular septum, thereby causing ventricular dyssynchrony. This sequence of activation results in an uncoordinated contraction, which does not occur during biventricular activation through the natural conduction system of the heart. The cells of the natural conduction system may propagate an activation signal about four times faster than working myocardium. A cardiac rhythm or functional management device configured to pace the His bundle is an alternative to conventional ventricular pacing. His-bundle pacing (HBP) may activate the heart's natural conduction system, including the left and right bundle branches and Purkinje fibers, and thereby restore or maintain efficient and coordinated cardiac response. This may reduce or eliminate the potential long-term harmful hemodynamic effects associated with continuous RV apical pacing.

However, when not being successful, the HBP may not adequately restore cardiac synchrony. In some instances, the electrical stimulation may lose its ability to activate (or capture) the His bundle, but only activates the para-Hisian myocardium surrounding the His bundle. Stimulating muscles near the His bundle may cause dyssynchronous patterns similar to RV apical pacing. This undesirable outcome is referred to as para-Hisian capture. Simultaneous capture of the His bundle and para-Hisian muscle (also known as a non-selective His-bundle capture) may be as clinically effective as the His-bundle only capture (also known as a selective His-bundle capture, as the resultant ventricular activation and contraction is dominated by the more rapid conducting Purkinje system. Another undesirable outcome of HBP is known as a complete loss of capture (LOC), where the HBP pulses capture neither the para-Hisian myocardium nor the His bundle.

The ability of HBP to restore cardiac synchrony may also be dependent on the pacing site relative to the blockage site along the His-Purkinje system, such as at the His bundle or a bundle branch. Ventricular dyssynchrony in many heart failure (HF) patients may be attributed to various degrees of left bundle branch block (LBBB), which causes delayed LV depolarization lagging behind RV depolarization. Effective propagation of the action potentials through the His-Purkinje system to restore cardiac synchrony may be achieved only if the HBP pulses are delivered distal to the blockage site. If the HBP pulses are delivered proximal to the blockage site, even if the proximal portion of the His bundle is activated, the action potential cannot bypass the blockage and propagate to the ventricles through the His-Purkinje system. Consequently, no cardiac synchrony may be restored.

Atrioventricular (AV) conduction disturbance refers to abnormal conduction or obstruction (i.e., block) in the AV node or in the His-Purkinje system below the AV node. AV conduction disturbance can include different degrees of obstruction, varying from a mild delay in conduction (first-degree AV block) to a conduction block between atria and ventricles (second- and third-degree AV blocks). AV conduction disturbance can be functional in nature, or attributable to local disease in the physiologic conduction system. Conduction disturbance or blockage may occur at various sites of the physiologic conduction system, including AV node, the His bundle (the "intra-Hisian" conduction disturbance or block), or below the His bundle (referred to as "infra-Hisian" conduction disturbance or block). Infra-Hisian blocks may occur at the left or right bundle branches (referred to as "bundle branch block") or the fascicles of the left bundle branch (referred to as "fascicular block").

Often AV conduction disturbance are intermittent. For example, intra-Hisian block status may change over time. Several mechanisms have been implicated in the AV conduction disturbance, including changing autonomic tone and changes in coronary perfusion. Changes in patient health status and medication may trigger AV conduction disturbance. Some AV conduction disturbance may be rate-related, such as rate-dependent bundle branch block, in which the delay conduction or blockage only occurs at times of fast heart rates (e.g., above a critical heart rate), and diminishes at slower heart rates (e.g., below the critical heart rate). Myocardial ischemia or refractoriness of intra-Hisian or infra-Hisian fascicles at faster heart rates may cause rate-related AV conduction disturbance. Patients with rate-related AV conduction disturbance may experience dyssynchrony and symptoms during exertion and activities when their heart rates rise and exceed a cut-off heart rate that triggers conduction block. Many patients with intermittent or rate-related conduction disturbance ultimately develop permanent bundle branch block.

Because the success rate of HBP capture and its ability to restore cardiac synchrony may vary from patient to patient and are affected by many factors (e.g., pacing site, stimulation strength), and considering potential side effects attributable to HBP in some patients (e.g., phrenic nerve stimulation or pain sensation), it is desirable, at least in some instances, to limit the use of HBP only as a need arises, such as when patient AV conduction is compromised. The present inventors have recognized that there is an unmet need of an artificial pacing system or device that can automatically adapt the HBP therapy to an indication of rate-related or intermittent AV conduction disturbance. The present document describes various examples of systems, devices, and methods for providing conditional HBP in accordance with the presence of an indication of AV conduction disturbance. An exemplary medical system includes an AV conduction monitor to detect an indication of presence or absence of intermittent or rate-related AV conduction disturbance using physiologic information of the subject. In the event that an intermittent or rate-related AV conduction disturbance is present, a control circuit provides a control signal to an electrostimulation circuit to deliver HBP pulses. If there is no indication of intermittent or rate-related AV conduction disturbance, or a previously detected intermittent or rate-related AV conduction disturbance has been terminated, the control circuit withholds or discontinues delivery of the HBP pulses to promote intrinsic ventricular conduction and activation, such as produced by sinus node or natural or paced atrial activations that propagate to the ventricles.

The systems, devices, and methods discussed in this document may improve the technology of cardiac pacing for patients with cardiac disease, such as HF with intermittent or rate-related conduction disturbance, yet with little to no additional cost or system complexity. HBP may activate natural His-Purkinje system, thereby preserving ventricular synchrony and improving cardiac performance without structural and functional impairment to the heart. HBP as discussed in the present document can leverage the electrophysiology of the His bundle region, and improve pacing efficiency utilizing the natural conduction mechanisms of the heart, while reducing long-term harmful hemodynamic effects associated with conventional RV apical pacing used for HF management. Compared to conventional permanent HBP, the subject matter discussed herein takes into consideration that some AV conduction disturbances (e.g., intra-Hisian block) are more likely intermittent or rate-related, and advantageously adapts HBP delivery to a detected indication of presence or absence of AV conduction disturbance, thus more efficiently uses the HBP therapy only when necessary. Withholding or discontinuing HBP whenever, and for as long as, the indication of AV conduction disturbance is absent may not only avoid unnecessary HBP therapy and therefore eliminating potential side effects of HBP (e.g., phrenic nerve stimulation or pain sensation), but also promote intrinsic ventricular activation via patient native normal His-Purkinje system, which can result in more favorable ventricular performance and hemodynamic outcome than artificial cardiac pacing such as HBP. Considering the high prevalence of intermittent or rate-related conduction disturbance in HF patient population, the conditional HBP discussed herein may potentially benefit many HF patients with intermittent or rate-related AV blocks. Additionally, compared to conventional permanent HBP, a pacing system or device implemented with the conditional HBP discussed herein may deliver less HBP therapies. This may advantageously save battery power of an artificial pacing system or device, extend device longevity, and make it possible to reduce device size (e.g., with smaller batteries or capacitors) without sacrificing existing performance metrics. As such, the subject matter discussed in this document improves the functionality of an artificial pacing system or device.

While His-bundle pacing is specifically discussed in this document, this is meant only by way of example and not limitation. It is within the contemplation of the inventors, and within the scope of this document, that the systems, devices, and methods discussed herein (e.g., conditional pacing in response to an indication of presence of absence of intermittent or rate-related conduction disturbance) may be applied to controllably stimulate right or left bundle branches or fascicles, the Purkinje fibers, among other conductive cardiac tissue.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, percutaneously, or minimally invasive placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG. 1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-112B, are positioned in or on a His bundle 121, a region distal to the blocked or slowly conducting AV node and in the AV septum, an interventricular septum region, or a right atrial region near the His-bundle 121. Alternatively, one or more of the electrodes 112A-112B, or other electrodes on the lead 106, can be configured to stimulate a bundle branch, such as a left bundle branch or a right bundle branch. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-112B, are positioned at or near other parts of the natural conduction pathways, such as one of the bundle branches 122 or 123, the Purkinje fibers 124, or other conductive tissue, in addition to or in lieu of a region at or near the His bundle 121.

In an example, the lead 106 may be a single pass lead having a plurality electrodes for stimulating multiple cardiac sites, including electrodes disposed at or near the His bundle (e.g., the electrodes 112A-112B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. In some examples, the cardiac disease management system 100 may include one or more leadless stimulators/sensors untethered to a lead and in wireless communication with the IMB 104. The leadless stimulators/sensors may deliver electrostimulation, sense a physiological signal, such as cardiac electrical signals in response to cardiac stimulation, and transmit the sensed data to the IMD 104.

The IMB 104 may include a hermetically sealed housing 116 that houses one or more of an electrostimulation circuit, a sensing circuit, a control circuit, a communication circuit, and a battery, among other components. In an example, the IMB 104 includes a His-bundle pacing system 118 configured to generate His-bundle pacing (HBP) pulses to stimulate the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-112B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or multipolar (e.g., bipolar or quadripolar) His-bundle pacing may be selected by a system user from a plurality of candidate electrodes from a given lead or multiple separate leads comprising the pacing system, and programmed into the His-bundle pacing system 118. In some examples, HBP pulses may be provide by a leadless device, such as a leadless cardiac pacemakers (LCP). One or more electrodes may be distributed on the body of the LCP and in contact with His-bundle region to deliver the HBP pulses.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, a heart rate or a pulse rate signal, a thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a cardiac acceleration signal, a heart sound signal, an intracardiac acceleration signal, a respiration signal, or a physical activity or exertion level signal, a cardiac timing signal, among others. In some examples, the His-bundle pacing system 118 may sense far-field ventricular activation (FFVA) using one or more electrodes or a physiologic sensor. The FFVA may be a signal recorded from afar at a given moment in time by two electrodes having similar source impedance. The FFVA may be sensed in response to electrostimulation to the His bundle or a bundle branch. In an example, the FFVA includes an EGM sensed via an electrode positioned within, or on the epicardial surface of, a ventricle. In an example as illustrated in the FIG. 1, the lead system may include a ventricular lead 107 including at least one RV electrode 131, which may be a tip electrode, a ring electrode, or a coil electrode. The His-bundle pacing system 118 may sense a FFVA signal (e.g., a far-field EGM) using the RV electrode 131 (e.g., as a cathode) and a reference electrode (e.g., as an anode). The EGM sensed as such using an RV electrode represents far-field LV activation, or far-field BiV activation. In an example, the reference electrode is a proximal electrode 132 on the ventricular lead 107. The proximal electrode 132 may be a coil electrode situated at the superior vena cava (SVC) of the heart. The distal electrode 131 and the proximal electrode 132 may also be used to deliver defibrillation shocks to correct ventricular tachyarrhythmia. In an example, the reference electrode may include the housing 116 or an electrode therein. In another example, the FFVA signal may be sensed using an atrial electrode 111 associated with the lead 106 and positioned in the RA and a reference electrode. In yet another example, the FFVA signal may be sensed using a His-bundle electrode associated with the lead 106 (e.g., electrode 112A or 112B) and a reference electrode. Examples of the reference electrode may include the housing 116 or an electrode therein. In another example, the FFVA signal may include a subcutaneous ECG signal sensed using subcutaneous chest electrodes such as located at the housing 116. In yet another example, the FFVA signal may include surface ECG signal sensed using skin electrodes attached to the body surface.

The His-bundle pacing system 118 may include electrostimulation circuitry configured to stimulate a patient physiologic conduction pathway (e.g., His bundle or a part of a bundle branch), restore cardiac synchrony, and therefore improve cardiac performance. The His-bundle pacing system 118 may include a conduction monitor to monitor atrioventricular (AV) conduction status, and to detect an indication of presence or absence of rate-related or intermittent AV conduction disturbance. A control circuit may provide a control signal to the electrostimulation circuitry to control the delivery of HBP, such as enabling HBP delivery only if an indication of presence of rate-related or intermittent AV conduction disturbance is detected, and disabling HBP delivery in response to an indication of absence of rate-related or intermittent AV conduction disturbance to promote ventricular activation through the natural electrical conduction pathways. In various examples, the His-bundle pacing system 118 may additionally provide ventricular backup pacing (VBP) if the HBP does not capture the His-bundle and activate the ventricles.

The IMB 104 may communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMB 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMB 104. In various embodiments, the external system 140 may include a user interface to display received information to the user, and receive user input for operation control of the IMD 104. In an example, the external system 140 can be configured to verify pacing capture status, perform pacing threshold test to determine an HBP threshold. The capture verification and threshold testing may be executed periodically, or triggered by a specific event such as a user command. A user may use the external system 140 to program the IMB 104, such as to configure a pacing vector (e.g., specifying anode and cathode electrodes) to deliver HBP, or to configure a sense vector to sense a physiological signal.

The external system 140 may include a remote device in a location relatively distant from the IMD 104 and in communication with the proximal external device via a telecommunication network. The remote device may evaluate collected patient data and provide alert notifications, among other possible functions. In an example, the remote device may include a centralized server acting as a central hub for collected patient data storage and analysis. The server can be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMB 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, capture verification, or AV conduction status, among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
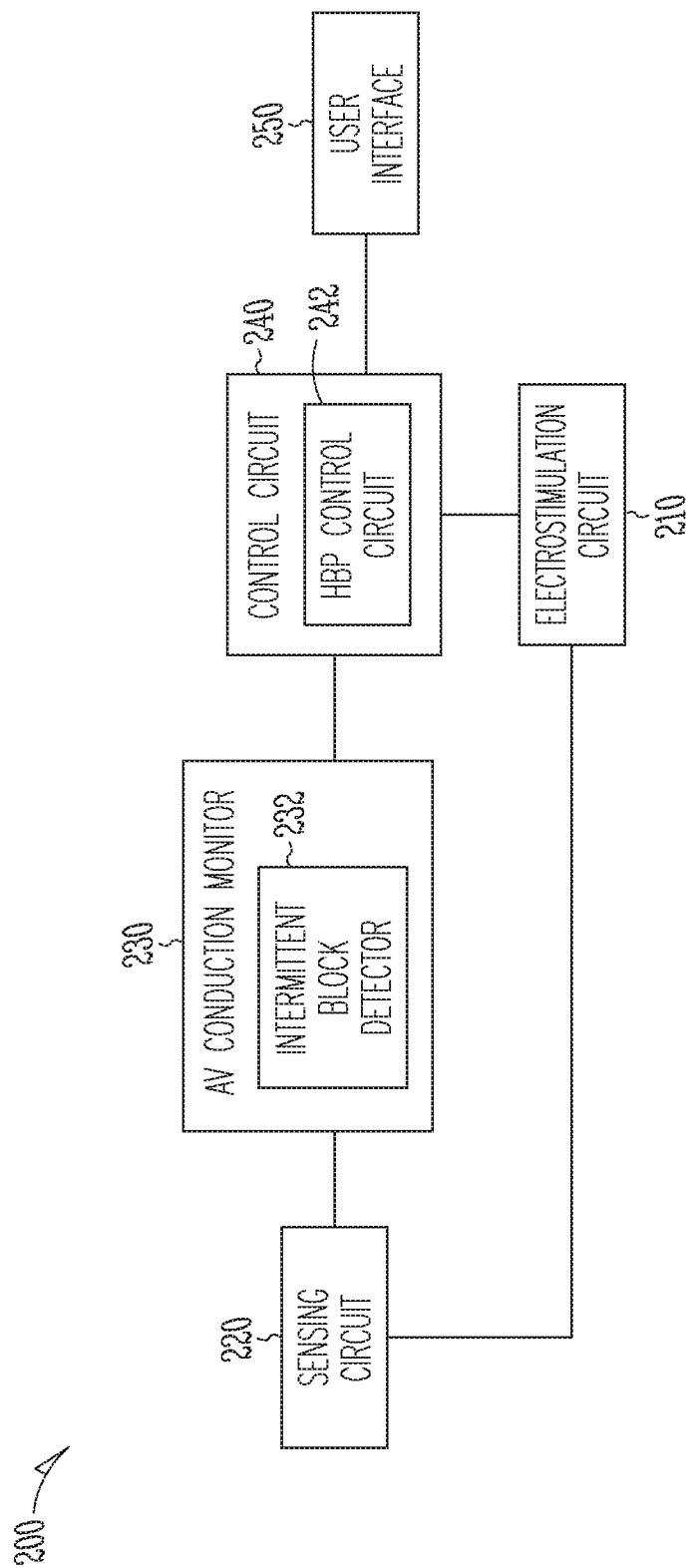
FIG. 2 is a block diagram illustrating an example of portions of an HBP system configured to provide conditional HBP.

FIG. 2 is a block diagram illustrating an embodiment of portions of a His-bundle pacing system 200 configured to provide conditional HBP. The His-bundle pacing system 200 represents an embodiment of the His-bundle pacing system 118, and may include an electrostimulation circuit 210, a sensing circuit 220, an atrioventricular (AV) conduction monitor 230, a control circuit 240, and a user interface 250.

The electrostimulation circuit 210 can be configured to generate stimulation energy for delivery to the heart 102, such as via one or more leads and the associated electrodes. The electrostimulation circuit 210 can be configured to generate His-bundle pacing (HBP) pulses for delivery to a target pacing site at or near the His bundle or a bundle branch along the conduction pathway, such as via the lead 106 and one or more of the electrodes 112A-112B. The target site may include an interventricular septum region or a right atrial region near the His-bundle, or other conductive tissue on the physiologic conduction pathway, such as right or left bundle branches or fascicles, or Purkinje fibers. In an example, the HBP pulses may be delivered in multiple cardiac cycles, such that at least one pulse is delivered within each of the multiple cardiac cycles. In various examples, the electrostimulation circuit 210 may additionally generate electrostimulation to stimulate non-cardiac tissue, such as nerve tissue, muscle tissue, or other excitable tissue.

The electrostimulation circuit 210 may generate HBP pulses according to one or more stimulation parameters such as provided by control circuit 240. Examples of the stimulation parameters may include information about stimulation site, stimulation strength, stimulation mode, or stimulation timing, among other parameters. Stimulation site includes information about pacing site, pacing vector configuration (e.g., anode and cathode electrodes), unipolar or bipolar pacing, etc. Stimulation strength parameters determine the amount of energy delivered to the pacing site, and may include pulse amplitude, pulse width, pulse frequency, pulse waveform, duty cycle, or stimulation duration. In some examples, the stimulation parameters may include one or more HBP parameters such as pacing rate, pacing interval, or timing of HBP pulses, among other parameters, which are collectively referred to as HBP configuration in this document.

Stimulation mode includes, by way of example and not limitation, a His-bundle only mode, an atrial-Hisian (AH) pacing mode, a His-ventricular (HV) pacing mode, or an atrial-His-ventricular (AHV) pacing mode. In the His-bundle only pacing mode, atrial activation may be sensed by the His-bundle pacing electrode, such as by using a single pass lead, or a leadless pacemaker having a form factor with multiple electrodes positioned such that reliable atrial sensing may be achieved. In the AH pacing mode, the HBP pulses may be delivered only when intrinsic atrial activation (AS), or atrial pacing (AP), fails to produce propagatable depolarization of the AV node and the His bundle. The AH pacing mode may be suitable for patients with varying degrees of heart block or sick sinus syndrome. The HV pacing mode involves sequential pacing of the His bundle and the ventricle. The ventricular pacing may be provided in a demand mode, such that the ventricular pacing pulses are delivered only when the His pacing fails to produce propagatable depolarization of the ventricles. The HV pacing mode may be indicated for patients with persistent or chronic atrial fibrillation, or who have been treated with atrioventricular node ablation or drugs to slow and the rapid ventricular rhythm that often results and allow HBP to predominate. The AHV pacing mode involves sequential atrial, Hisian, and ventricular pacing. One or more of the His-bundle pacing or the ventricular pacing may be delivered in a demand mode. The AHV pacing mode may be indicated for patients with cardiac dyssynchrony and having received cardiac resynchronization therapy, patients suffering from HF with LBBB, HF induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an AS or an AP event. An AH timing represents a latency period, within a cardiac cycle, from an intrinsic AS event or an AP event to the delivery of an HBP pulse. In demand HV pacing mode, the ventricular pacing pulses are timed relative to a His pacing event. The HV timing represents a latency period, within a cardiac cycle, from a His bundle event (e.g., an HBP pulse) to the delivery of ventricular pacing pulse. In an example, if an HBP pulse fails to induce ventricular depolarization, a backup ventricular pacing may be delivered at the end of the HV timing.

The electrostimulation circuit 210 can be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP, selective HBP causes only the excitation (depolarization) of the His bundle, without direct excitation of para-Hisian myocardium adjacent to the His bundle. Non-selective HBP directly causes excitation of both the His bundle and the para-Hisian myocardium. If the HBP pulses cause only excitation of the para-Hisian myocardium or other unintended cardiac tissue, without direct excitation of the His-bundle fibers, then a para-Hisian pacing results. If no tissue excitation is induced by HBP (e.g., neither the para-Hisian myocardium capture nor the His-bundle capture), then a complete loss of capture (LOC) results.

In addition to HBP, the electrostimulation circuit 210 can be configured to generate one or more of other pacing modalities, such as bradycardia ventricular demand pacing (VDP), cardiac resynchronization therapy (CRT), BiV pacing, or synchronized left ventricle (LV)-only pacing, single site pacing of only one site of a heart chamber (e.g., the left ventricle), or multisite pacing (MSP) of two or more sites of a heart chamber within the same cardiac cycle, among others. These pacing modalities may be delivered according to their respective stimulation strength, stimulation site, stimulation mode, or stimulation timing, among other parameters, such as provided by control circuit 240. In some examples, the electrostimulation circuit 210 may generate ventricular backup pacing (VBP) if HBP does not capture the excitable tissue and activate the ventricles. The VBP pulses may be delivered to a target ventricular site via electrodes disposed on a ventricular lead. Additionally or alternatively, backup pacing may be delivered to the His bundle via electrodes on a His-bundle pacing lead. In an example, VBP may include high-output pacing (HOP) pulses with higher pacing energy than conventional pacing pulses. The HOP pulse may be a biphasic or multiphasic waveform. In an example, the HOP pulse may have a peak-to-peak voltage amplitude of 5-8 volts, and a pulse duration of 50-70 msec. With higher amount of energy delivered to the myocardium, the HOP pulse may increase myocardial contractility and improve systolic function. However, chronic HOP pacing may overstress the heart and potentially be hazardous in some heart failure patients. According, in some examples, the HOP pulses may be delivered on an intermittent basis, such that the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al. U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

The sensing circuit 220 may be coupled to one or more electrodes or physiologic sensors to sense a physiologic signal. The physiologic signal may be sensed in the absence of pacing therapy, or during a pacing therapy, such as HBP. Examples of the sensed signals may include an electrocardiogram (ECG), an electrogram (EGM) of a portion of the heart such as atrial EGM, ventricular EGM, or evoked His potential, a heart rate or a pulse rate signal, an impedance signal, a cardiac acceleration signal, a heart sound signal, or a pressure signal, a cardiac timing signal, among other physiological or hemodynamic signals. In some examples, the sensing circuit 220 may sense a far-field ventricular activation (FFVA) signal. The FFVA signal may include a far-field electrical signal (e.g., an electrogram) indicative of electrical synchrony of depolarizations of the left and right ventricles. The far-field EGM may be sensed using a unipolar or a bipolar configuration. In an example, the far-field EGM may be sensed via a ventricular electrode positioned within or on the epicardial surface of an RV or LV, such as the distal electrode 131 on the ventricular lead 107 as shown in FIG. 1. In various examples, the far-field EGM may be sensed between the ventricular electrode 131 and the proximal electrode 132, between the ventricular electrode 131 and the housing 116 or an electrode therein, or between the ventricular electrode 131 and a joint electrode comprising the proximal electrode 132 and the housing 116 or an electrode therein that are at least temporarily electrically tied together. Such far-field EGMs sensed using the ventricular electrode 131 may represents far-field LV or far-field BiV (i.e., LV and RV) activations, as well as ventricular synchrony such as indicated by QRS width or interventricular conduction delay. Additionally or alternatively, the FFVA signal may be sensed using electrodes positioned in or on other heart chambers or locations other than RV and LV. In an example, the FFVA signal may be sensed using an atrial electrode, such as the RA electrode 111 associated with the lead 106, and a reference electrode such as the housing 116 or an electrode therein. In yet another example, the FFVA signal may be sensed using electrodes positioned in or on a His-bundle region, such as one of the electrodes 112A-112B associated with the lead 106, and a reference electrode such as the housing 116 or an electrode therein. In yet another example, the FFVA signal may include a subcutaneous ECG signal sensed using chest electrodes such as located at the housing 116. Such FFVA signal may contain information about ventricular synchrony, such as QRS width or interventricular conduction delay. In some examples, the FFVA signal may include a mechanical signal indicative of mechanical synchrony of contractions and vibrations between of the left and right ventricles. Examples of the mechanical signal may include an impedance signal, a heart sound signal, a pressure signal, among other hemodynamic signals that may be sensed using a physiologic sensor.

The AV conduction monitor 230 can be configured to detect an indication of presence or absence of intermittent or rate-related conduction disturbance using the physiologic information of the patient, such as one or more physiologic signals received by the sensing circuit 220. An intermittent AV conduction disturbance is characterized by blockage status that changes over time, such as due to patient condition or medication. A rate-related AV conduction disturbance, such a rate-related LBBB, is characterized by delayed or blocked AV conduction only at times of when the heart rate is above a heart rate cutoff Intermittent or rate-related AV conduction abnormality can often be found in patients with intra-Hisian blocks. The detection of the indication of presence or absence of intermittent or rate-related conduction disturbance can be based on heart rate, QRS width, among other physiologic parameters generated from the received physiologic sensor signals. In an example, the detection of intermittent or rate-related conduction disturbance may be carried out while the heart is being paced, such as during delivery of HBP due to a previous detection of intermittent or rate-related conduction block. For example, the AV conduction monitor 230 may sense a heart rate from an atrium and determines whether the intermittent or rate-related conduction block persists or has terminated, without interruption or suspension of an ongoing HBP delivery. Alternatively, HBP may be suspended for a specified period to allow for an assessment of the conduction block status. When the HBP is suspended, the system may operate in a sense-only mode where no cardiac pacing is delivered by the electrostimulation circuit 210. In an example, during the delivery of HBP, the AV conduction monitor 230 may continuously scan for resumption of normal conduction, such as when heart rate falls below a heart rate cutoff ($HR_{block}$) at which block has occurred. In another example, the AV conduction monitor 230 may search for resumption of normal conduction periodically (e.g., every 10 minutes). Periodic search may be used if the AV conduction disturbance is a paroxysmal block. In an example, the periodic search may entail suspending HBP temporarily and determining whether normal conduction has resumed. If AV conduction disturbance persists, HBP can be resumed at appropriate AHI (e.g., approximately 50-120 msec) following an AS or an AP event. Examples of detecting an indication of presence or absence of intermittent or rate-related conduction disturbance are discussed below, such as with reference to FIG. 3 below.

In some examples, the AV conduction monitor 230 may determine a heart rate cutoff ($HR_{block}$) that triggers development of intermittent or rate-related conduction disturbance. The heart rate cutoff $HR_{block}$ can vary from patient to patient. In some patients, conduction disturbance (e.g., LBBB) may occur at relatively slow heart rate (e.g., 70-80 bpm), resulting in dyssynchrony with activities of daily living. In some other patients, however, the $HR_{block}$ can be as high as 100-120 bpm. The heart rate cutoff ($HR_{block}$) may also be variable in the same patient at different times (e.g., vary from 70 bpm to 110 bpm). The AV conduction monitor 230 may monitor heart rate and/or other physiologic parameters continuously or periodically, determine an individualized $HR_{block}$, and update an existing $HR_{block}$ of the patient as needed, examples of which are discussed further with reference to FIG. 3.

The control circuit 240 can be configured to selectively activate or deactivate a pacing modality in accordance with the detected indication of presence or absence of intermittent or rate-related conduction disturbance. In an example, the control circuit 240 may be implemented as a part of a microprocessor circuit in the cardiac disease management system 100. The microprocessor circuit may be a dedicated processor such as a digital signal processor, application specific integrated circuit (ASIC), microprocessor, or other type of processor for processing information including heart sounds. Alternatively, the microprocessor circuit may be a general-purpose processor that may receive and execute instructions of performing the functions, methods, or techniques described herein.

As illustrated in FIG. 2, the control circuit 240 may include circuit sets that, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The control circuit 240 may include an HBP control circuit 242 to control the electrostimulation circuit 210 to generate HBP pulses. In an example, the HBP control circuit 242 may provide a control signal to the electrostimulation circuit 210 to deliver HBP pulses to stimulate the physiologic conduction pathway in response to a detected indication of presence of intermittent or rate-related AV conduction disturbance of the heart, or withhold or discontinue delivery of the HBP pulses in response to a detected indication of absence of intermittent or rate-related AV conduction disturbance. The HBP control circuit 242 may adjust one or more stimulation parameters, such as a pulse amplitude, a pulse width, a pulse rate, a pulse shape or waveform, a duty cycle, or a stimulation duration, among others, according to the detected AV conduction status. Additionally or alternatively, the HBP control circuit 242 may adjust stimulation delivery timing, or a stimulation site for delivering respective pacing pulses (e.g., switching to a different stimulation vector), according to the detected AV conduction status. For example, according to some examples, in response to an indication of a presence of intermittent or rate-related AV conduction disturbance, the HBP control circuit 242 may deliver HBP pulses at an atrio-Hisian interval (AHI) following an AS or an AP event. The AHI can be consistent with a normal AH interval of the patient. The AHI can be a programmable value. In an example, the AHI can be approximately 50-120 msec.

In some examples, the control circuit 240 controls the electrostimulation circuit 210 to deliver one or more modalities of cardiac stimulation other than HBP, such as bradycardia pacing, CRT, BiV pacing, LV-only pacing, multisite pacing (MSP) of two or more sites of a heart chamber (e.g., LV) within the same cardiac cycle, etc. In an example, the control circuit 240 may include a backup pacing control circuit (not shown) to control the electrostimulation circuit 210 to deliver ventricular backup pacing (VBP) if HBP fails to capture the physiologic conduction pathway and elicit ventricular activation. In an example, VBP pulses can be delivered at the expiration of the atrioventricular delay ($AVD_B$) with respect to an AS or an AP event if no ventricular activation is detected within the $AVD_B$, or alternatively deliver VBP pulses at the expiration of a His-to-ventricular delay ($HVD_B$) with respect to the HBP pulse delivery if no ventricular activation is detected within the $HVD_B$.

The user interface 250 may include an input unit and an output unit. At least a portion of the user interface 250 may be implemented in the external system 140. The input unit may receive user input such as values of the parameters for physiologic event sensing, heart rate cutoff $HR_{block}$ for detecting a rate-related AV conduction disturbance, thresholds for signal metrics used for detecting an intermittent AV conduction disturbance, stimulation parameters (pulse amplitude, pulse width, pulse rate, etc.) for HBP, or for other pacing modalities (e.g., VBP), among others. The input unit may receive user programming of stimulation parameters, or confirmation, rejection, or otherwise modification of the stimulation parameters generated by the control circuit 240. The input unit may include an input device such as a keyboard, on-screen keyboard, mouse, trackball, touchpad, touch-screen, or other pointing or navigating devices.

The output unit may include circuitry configured to generate a human-perceptible notification of the detected conduction disturbance such as an indication of occurrence of rate-related or intermittent AV conduction disturbance. The output unit may be coupled to a display for displaying the received physiologic signals (e.g., ECG, EGMs, FFVA signals, among other signals), event sensing information such as atrial, ventricular, or His-bundle events, and timing information of the sensed events. The event sensing information may be overlaid with the signal tracings, or be displayed in a separate marker channel. The stimulation parameters, and intermediate measurements or computations may also be displayed. The output unit may be coupled to a printer for printing hard copies of information about the event detection and therapy titration protocol. The information may be presented in a table, a chart, a diagram, or any other types of textual, tabular, or graphical presentation formats. The presentation of the output information may include audio or other media formats. In an example, the output unit may generate alerts, alarms, emergency calls, or other forms of warnings to signal the system user about the AV conduction status, His-bundle capture status, change of pacing modalities, or adjustment of stimulation parameters. In an example, the output unit may generate an alert when a loss of capture is indicated and VBP is delivered. In another example, frequent VBP may trigger the output unit to generate an alert and prompt a user (e.g., a clinician) to reprogram the pacing system.

Portions of the His-bundle pacing system 200 may be implemented distributedly between two devices. In an example, a first device may include the electrostimulation circuit 210 and a stimulation delivery system such as the lead and associated electrodes for delivering the HBP pulses, and a second device may include the sensing circuit 220 and at least a portion of the control circuit 240. The sensing circuit 220 of the second device can be configured to sense, among other signals, the far-field ventricular response to the HBP pulses. In an example, the first and second devices are both implantable devices. In another example, at least one of the first or the second device is a non-implantable, wearable device.

Figure 3:
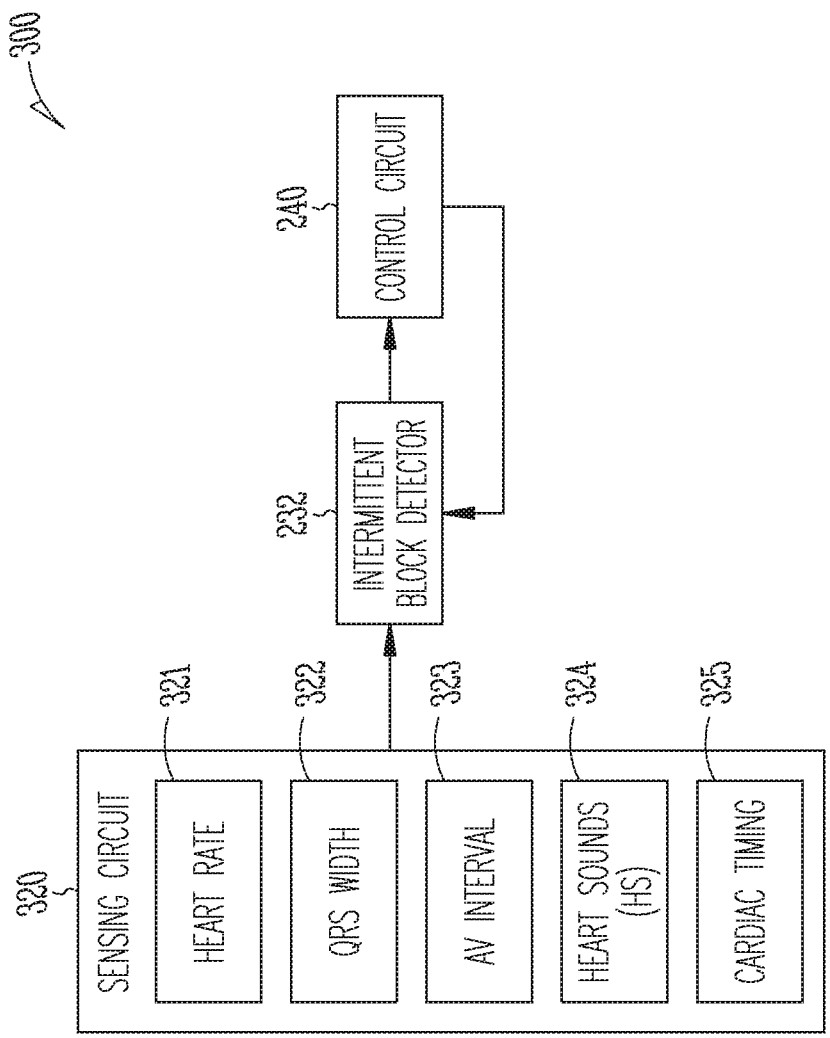
FIG. 3 is a block diagram illustrating an example of portions of an HBP system configured to control delivery of HBP according to a detection of rate-related or intermittent AV conduction disturbance.

FIG. 3 is a block diagram illustrating generally an example of portions of an HBP system 300 configured to control delivery of HBP according to a detection of rate-related or intermittent AV conduction disturbance. The system portion 300 may be an embodiment of part of the His-bundle pacing system 200. As illustrated in FIG. 3, the system portion 300 can include a sensing circuit 320, which can be an embodiment of the sensing circuit 220, and the AV conduction monitor 230 and the control circuit 240 as shown in FIG. 2.

The sensing circuit 320 can be configured to sense from sensors, or receive from data storage, physiologic information of a patient. By way of example and not limitation, the physiologic information may include heart rate information 321, QRS width information 322, atrioventricular (AV) interval information 323, heart sounds (HS) information 324, and cardiac timing information 325. The heart rate information 321 may be determined from a cardiac electrical signal, a cardiac mechanical signal, or a physiologic signal that contains information of pulsatile cardiac activity (e.g., a pulse rate signal, a blood pressure signal, among others). Because the rate-related conduction block (e.g., rate-dependent LBBB) occurs only at higher heart rates (e.g., exceeds the rate cutoff $HR_{block}$), a close monitoring of patient heart rate may help determine when a rate-related block has occurred. The AV conduction monitor 230 may compare the heart rate information 321 to a threshold value such as the heart rate cutoff $HR_{block}$ (or a function of the $HR_{block}$), detect an indication of a presence of rate-related AV conduction disturbance if the heart rate information 321 exceeds the rate cutoff $HR_{block}$, and detect an indication of an absence of intermittent or rate-related AV conduction disturbance if the heart rate information 321 is below the rate cutoff $HR_{block}$. The $HR_{block}$ can be individually determined for a patient, such as based on the conduction and block data from patient history. A personalized $HR_{block}$ can better address the inter-subject variability of $HR_{block}$ in AV conduction disturbance patients. The personalized $HR_{block}$ may be updated periodically, or triggered by an event such as a change in patient health status or medication. In an example, the determination or update of a personalized $HR_{block}$ may be based on physiological information (e.g., QRS width information 322, heart sounds information 323, or cardiac timing information 324), as to be discussed further below.

In various examples, the heart rate information 321 includes an atrial heart rate, such as an atrial intrinsic rate (that is, atrial sensed (AS) rate, or sinus rate), or an atrial pacing (AP) rate. The atrial heart rate can be determined using the P wave or atrial pacing event sensed from an ECG, or an atrium EGM. The atrial EGM may be sensed using the atrial electrode 111 as illustrated in FIG. 1, or using an atrial electrode associated with a separate lead or catheter other than the lead 106 (not shown). In another example, atrial heart rate may be a far-field atrial heart rate sensed from an electrode outside the atrium configured to sense an electrical signature in the far field of atrium, such as the proximal electrode 132 on the ventricular lead 107. In yet another example, atrial heart rate may include a sensor-driven atrial pacing rate. The sensor may be associated with an adaptive pacing device (e.g., a pacemaker) configured to detect patient physiologic responses or indications of metabolic demand using sensors. Examples of the sensors may include an activity sensor (e.g., an accelerometer) to sense physical activity, a respiration sensor (e.g., a thoracic impedance sensor) to sense respiration rate, tidal volume, respiration pattern, among other respiratory parameters. A sensor-driven atrial pacing rate may be determined according to the patient physiologic responses. The sensor-driven atrial pacing rate represents an estimated heart rate during exertion or activity, and may be used to determine a presence of rate-related AV conduction disturbance.

Because atrial heart rate is generally less likely to be interfered by HBP than ventricular heart rate, the AV conduction monitor 230 may assess conduction status using the atrial heart rate without interrupting or suspending an ongoing HBP therapy. The AV conduction monitor 230 may compare the heart rate information 321 to the heart rate cutoff $HR_{block}$ to determine whether the atrial heart rate has changed. If the atrial heart rate falls below the cutoff $HR_{block}$, then the AV conduction monitor 230 determines that the intermittent or rate-related AV block has termination or improved. In response, the HBP control circuit 242 may generate a control signal to the electrostimulation circuit 210 to discontinue the HBP therapy.

The QRS width information 322 may be derived from a surface ECG signal, a subcutaneous ECG signal, a ventricular EGM (e.g., between RV electrode 131 and a reference electrode such as the housing 116, or between the RV electrode 131 and a proximal electrode 132), or a FFVA signal as discussed above. The AV conduction monitor 230 may detect an indication of a presence of intermittent AV conduction disturbance in response to the QRS width metric exceeding a QRS width threshold ($QRS_{block}$), and detect an indication of an absence of intermittent AV conduction disturbance in response to the QRS width metric falling below the $QRS_{block}$. The $QRS_{block}$ may be user-programmable. In an example, the $QRS_{block}$ is approximately 80-120 msec. In another example, the $QRS_{block}$ is approximately 150-200 msec. In some examples, the $QRS_{block}$ may be individually determined for a patient, such as based on the conduction and block data from patient history.

The atrioventricular interval (AVI) 323 represents an atrioventricular conduction time, and can be measured from an ECG as P wave to R wave interval (P-R interval). Alternatively, the AVI can be measured between (i) an atrial sensed event (AS, representing a sinus node activation) or an atrial paced event (AP) and (ii) a ventricular sensed event (VS) within a same cardiac cycle. These events may be detected from a surface ECG, or from an intracardiac EGM (e.g., an atrial EGM sensed between the atrial electrode 111 and the housing 116, or a ventricular EGM sensed between the RV electrode 131 and the housing 116). The AV conduction monitor 230 can detect an indication of a presence of intermittent AV conduction disturbance in response to the AVI exceeding an AVI threshold ($AVI_{block}$), and detect an indication of an absence of intermittent AV conduction disturbance in response to the AVI falling below the $AVI_{block}$. The $AVI_{block}$ may be user-programmable. In an example, the $AVI_{block}$ is approximately 180 msec. In another example, the $AVI_{block}$ is approximately 200 msec. Similar to the personalized $QRS_{block}$, the $AVI_{block}$ can be individually determined for a patient, such as based on the conduction and block data from patient history.

The HS information 324 is indicative of acoustic or vibrational activity of a heart, and may be sensed using an accelerometer, an acoustic sensor, a microphone, a piezo-based sensor, or other vibrational or acoustic sensors. Such sensors may be implantable, wearable, holdable, or otherwise ambulatory sensors, and placed external to the patient or implanted inside the body. In an example, a HS sensor may be included in at least one part of an ambulatory system, such as the AMD 104, or a lead (e.g., the lead 106 or the lead 107) coupled to the ambulatory system. Examples of the HS information 324 may include one or more of a first (S1) heart sound, a second (S2) heart sound, a third (S3) heart sound, or a fourth (S4) heart sound components. HS components may be detected using respective HS detection windows. The HS detection windows can be determined with reference to a physiologic event such as R wave, Q wave, or QRS complexes obtained from an electrocardiogram or an intra-cardiac electrogram signal synchronously sensed with the HS signal. In an example, a HS component may be detected adaptively by tracking the temporal locations of the previously detected HS component. A HS metric, such as an intensity (e.g., amplitude or signal power under the curve), morphology, or duration of one or more HS components, may be used to characterize the AV synchrony and detect AV conduction disturbance. For example, an S1 intensity may be inversely related to a P-R interval. A short P-R interval corresponds to an accentuated S1, whereas a long P-R interval results in a soft S1. The AV conduction monitor 230 may detect an indication of a presence of intermittent AV conduction disturbance in response to a S1 intensity falling below an S1 intensity threshold ($S1_{block}$) (indicating a slow or delayed AV conduction), or detect an indication of an absence of intermittent AV conduction disturbance in response to an S1 intensity exceeding $S1_{block}$. $S1_{block}$ may be user-programmable.

The cardiac timing information 325 represents electromechanical coupling of the heart, and may include timing parameters such as a pre-ejection period (PEP), a systolic timing interval (STI), a left-ventricular ejection time (LVET), or a diastolic timing interval (DTI), among others. The PEP represents the total duration of the electrical and mechanical events prior to ejection, and can be measured as the time duration from the onset of the QRS to the S1 heart sound. Alternatively, the PEP can be measured from the ventricular activation (ventricular sense or ventricular pacing) to the onset of S1 heart sound. The STI represents the duration of total electro-mechanical systole, and contains two major components, namely the PEP and the LVET. The STI can be measured as an interval from the onset of the QRS complex on the ECG, or the atrial activation event in an intracardiac EGM, to the onset of S2 heart sound. The DTI represents the duration of total electro-mechanical diastole. The DTI spans from the closure of the aortic valve to the onset of the atrial depolarization in the next cardiac cycle. In an example, the DTI can be measured as the interval from the S2 heart sound to the onset of the QRS complex on the ECG or the atrial activation event in an intracardiac EGM of the next cardiac cycle. In some examples, the cardiac timing information 325 may include composite measures using two or more of the STI, the DTI, the PEP, the cardiac cycle (CL), or the LVET. Examples of the composite measures can include PEP/LVET ratio, STI/DTI ratio, STU cycle length (CL) ratio, or DTI/CL ratio, among others. In an example, the AV conduction monitor 230 can detect an indication of a presence of intermittent AV conduction disturbance if the PEP is above a PEP threshold ($PEP_{block}$), or detects an indication of an absence of intermittent AV block if the PEP is below $PEP_{block}$. $PEP_{block}$ may be user-programmable. In an example, the $PEP_{block}$ is approximately 90-100 msec.

In some examples, the intermittent block detector 232 may detect either a presence or an absence of rate-related or intermittent AV conduction disturbance using two or more of the physiologic information 321-325. In an example, the intermittent block detector 232 may perform an initial detection of intermittent or rate-related AV conduction disturbance using at least one of the physiologic information 322-325. Heart rate information 321 may be continuously monitored during the initial detection. In response to the detection of an occurrence of intermittent or rate-related AV conduction disturbance, the instant heart rate can be determined as the heart rate cutoff $HR_{block}$ corresponding to development of the intermittent or rate-related AV conduction disturbance. The $HR_{block}$ may be reported to a user (e.g., a clinician) such as via the user interface 250. The control circuit 240 may provide the $HR_{block}$ to the AV conduction monitor 230 to update the existing heart rate cutoff for detecting rate-related AV conduction disturbance.

In another example, the intermittent block detector 232 may use a sequential detection comprising an initial detection based on HR information 321, followed by a confirmation using at least one of the physiologic parameters 322-325. Heart rate can be monitored continuously or periodically, and compared to a heart rate threshold, such as the $HR_{block}$ or a function of $HR_{block}$. The $HR_{block}$ may be a personalized threshold value determined empirically in some instances. When the monitored heart rate exceeds the heart rate threshold (such that the initial detection indicates a presence of rate-related or intermittent AV block), the control circuit 240 may trigger the AV conduction monitor 230 to confirm the detected presence of intermittent or rate-related AV conduction disturbance using at least one of the physiologic parameters 322-325.

In an example, the heart rate threshold $HR_{th}$ for initial heart rate comparison can be set to a value smaller than $HR_{block}$ (e.g., $HR_{th}=k*HR_{block}$ where $0<k<1$), such the initial HR-based detection is highly sensitive to potential events of intermittent or rate-related AV block. The confirmation by the subsequent detection based on one or more of physiologic parameters 322-325 may ensure a high specificity of detecting an intermittent or rate-related AV block. In an example, heart rates may be monitored continuously or periodically during the confirmation based on one or more of the physiologic parameters 322-325. A corrected heart rate cutoff ($cHR_{block}$) that corresponds to the confirmation of the presence of intermittent or rate-related AV block may be determined. The corrected heart rate cutoff ($cHR_{block}$) may be higher than the initial heart rate threshold $HR_{th}$. The $cHR_{block}$ may be reported to a user (e.g., a clinician) such as via the user interface 250. In some examples, the control circuit 240 may provide the $cHR_{block}$ to the AV conduction monitor 230, and replace the existing heart rate threshold $HR_{block}$ to detect future intermittent or rate-related AV conduction disturbance.

The sequential detection as discussed herein advantageously combines the detection powers of multiple physiologic information, and improves the sensitivity and specificity of detecting events of intermittent or rate-related AV conduction disturbance. The corrected heart rate cutoff ($cHR_{block}$) is a parameter of clinical significance that characterizes disturbance in a patient cardiac conduction system. With the $cHR_{block}$, detection of performance of intermittent or rate-related AV conduction disturbance can be improved, therapy or intervention can be timely and appropriately administered, unnecessary therapies can be avoided or reduced and device power can be saved. Accordingly, patient outcome and device functionally can both be improved.

Figure 4:
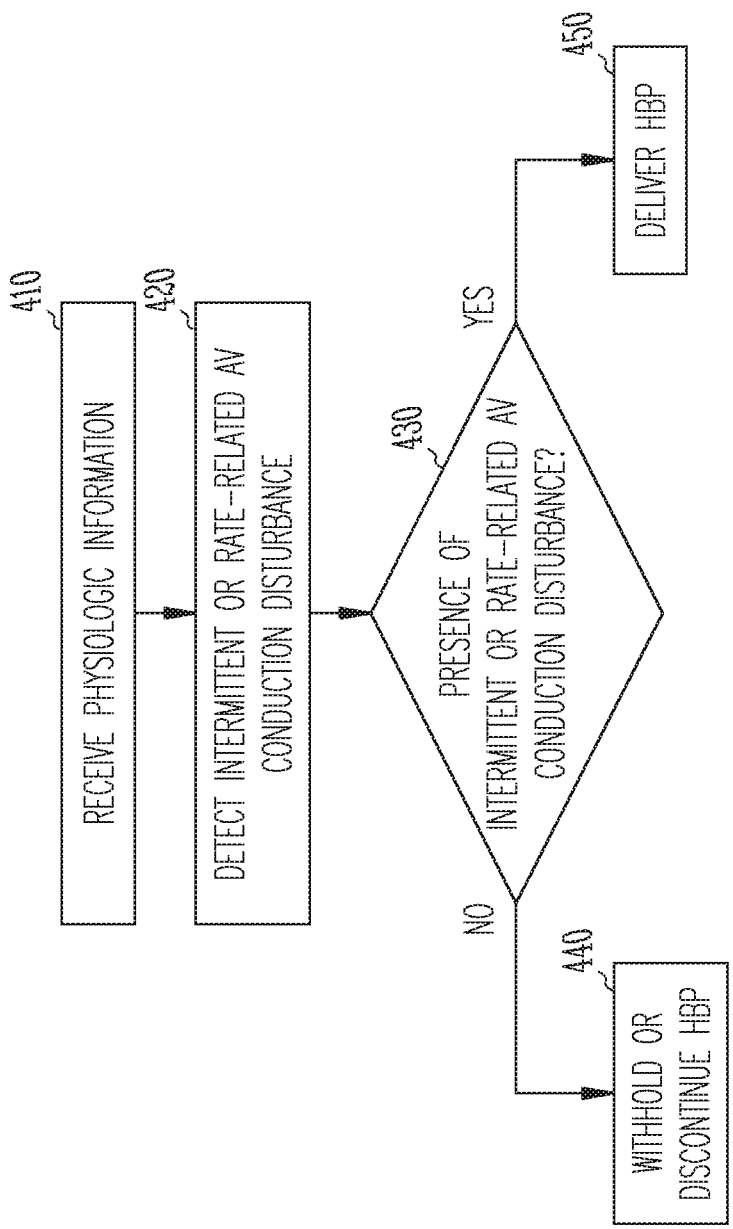
FIG. 4 is a flowchart illustrating generally an example of a method for providing His-bundle pacing (HBP) to correct rate-related or intermittent AV conduction abnormality in a patient using a medical-device system.

FIG. 4 is a flowchart illustrating generally an example of a method 400 for providing His-bundle pacing (HBP) to correct rate-related or intermittent AV conduction abnormality in a patient using a medical-device system. In particular, the method 400 may be used dynamically control HBP delivery (e.g., initiation or withholding of the HBP, and timing of the HBP delivery) based on patient AV conduction status. The method 400 may be implemented in and executed by an ambulatory medical device such as an implantable or wearable medical device, or in a remote patient management system. In an example, the method 400 may be implemented in, and executed by, the IMD 104, one or more devices in the external system 140, or the His-bundle pacing system 200.

The method 400 commences at 410, where physiologic information of a subject may be received. The physiologic signal may be sensed when no HBP is being delivered. Examples of the sensed signals may include an electrocardiogram (ECG), an electrogram (EGM) of a portion of the heart such as atrial EGM, ventricular EGM, or evoked His potential, a heart rate or a pulse rate signal, an impedance signal, a cardiac acceleration signal, a heart sound signal, or a pressure signal, a cardiac timing signal, among other physiological or hemodynamic signals. In some examples, the sensing circuit 220 may sense a far-field ventricular activation (FFVA) signal. The FFVA signal may include a far-field electrical signal (e.g., an electrogram) indicative of electrical synchrony of depolarizations of the left and right ventricles. In some examples, the FFVA signal may include a mechanical signal indicative of mechanical synchrony of contractions and vibrations between of the left and right ventricles.

At 420, AV conduction status may be monitored continuously or periodically, using the received physiologic information, to determine if an indication of intermittent or rate-related AV conduction disturbance is present or absent, such as using the AV conduction monitor 230. Various physiologic parameters may be determined from the received physiologic information, such as heart rate, QRS width, AV interval, heart sounds, or cardiac timing as illustrated in FIG. 3, among others. One or more of said physiologic parameters may be used to detect presence or absence of an indication of intermittent or rate-related AV conduction disturbance. For example, a rate-related AV conduction disturbance, such a rate-related LBBB, is characterized by delayed or blocked AV conduction only at times of when the heart rate is above a heart rate cutoff. At 420, a rate-related AV conduction disturbance is decided to be present if the patient heart rate exceeds a heart rate cutoff ($HR_{block}$), or to be absent if the patient heart rate is less than the $HR_{block}$. The $HR_{block}$ can vary from patient from patient, and from time to time in the same patient. An individualized $HR_{block}$ can be determined and updated as needed based on other sensor information, as to be discussed in the following with reference to FIG. 6. In an example, patient QRS width may be compared to a QRS width threshold ($QRS_{block}$). At 420, an intermittent AV conduction disturbance is decided to be present if the patient QRS width exceeds the $QRS_{block}$, or to be absent if the QRS width falls below the $QRS_{block}$. In an example, patient AVI may be compared to an AVI threshold ($AVI_{block}$). At 420, an intermittent AV conduction disturbance is decided to be present if the patient AVI exceeds the $AVI_{block}$, or to be absent if the patient AVI falls below the $AVI_{block}$. In an example, patient S1 intensity may be compared to an S1 intensity threshold ($S1_{block}$). At 420, an intermittent AV conduction disturbance is decided to be present if the patient S1 intensity falls below the $S1_{block}$, or to be absent if the S1 intensity exceeds the $S1_{block}$. In an example, a cardiac time interval may be determined, such as a pre-ejection period (PEP) representing a time duration from the onset of the QRS to the S1 heart sound. Patient PEP may be compared to a PEP threshold ($PEP_{block}$). At 420, an intermittent AV conduction disturbance is decided to be present if the PEP is above the $PEP_{block}$, or to be absent if the PEP is below the $PEP_{block}$.

If it is decided at 430 that no indication of intermittent or rate-related AV conduction disturbance is present, then at 440, the HBP may be withheld, or an ongoing HBP may be discontinued. Withholding or discontinuing HBP can promote cardiac conduction through the physiologic AV conduction system. This not only avoids or reduces unnecessary therapies (e.g., HBP or ventricular pacing), but may also bring about more favorable ventricular performance and hemodynamic outcome. Avoidance of unnecessary HBP can also conserve battery power and extend implantable device longevity. If it is decided at 430 that an indication of intermittent or rate-related AV conduction disturbance is present, then at 450 HBP may be delivered to the physiologic conduction pathway (e.g., His-bundle or a bundle branch). The HBP pulses may be delivered in accordance with stimulation waveform parameters, stimulation site, stimulation timing, among others. According to some examples, in response to an indication of a presence of intermittent or rate-related AV conduction disturbance, HBP pulses may be delivered at an atrio-Hisian interval (AHI) following an AS or an AP event. The AHI can be consistent with a normal AH interval of the patient. The AHI can be a programmable value. In an example, the AHI can be approximately 50-120 msec. In an example, at 450, the HBP waveform parameters and/or stimulation site may be programmed or adjusted by a user, or automatically determined or adjusted such as by the HBP control circuit 242. In some examples, the delivery of the HBP pulse may trigger a His capture verification process. If the HBP fails to capture the conduction pathway (e.g., loss of capture of para-Hisian capture), one or more HBP pacing parameters may be adjusted. In some examples, ventricular backup pacing (VBP) may be delivered if HBP fails to capture the physiologic conduction pathway and elicit ventricular activation.

In some examples, the method 400 may be used to determine whether a presently HBP therapy needs to be continued or discontinued. The received physiologic signal at 410 may be acquired while the patient undergoes HBP, representing patient physiologic response to HBP (e.g., heart rate response, or other physiologic responses as detected by physiologic sensors). An indication of a presence of intermittent or rate-related AV conduction disturbance may be detected at 420 using patient physiologic response to HBP. In an example of HR-based detection of intermittent or rate-related AV conduction disturbance, the heart rate can be represented by atrial heart rate. Because the atrial heart rate is less likely to be interfered by HBP than ventricular heart rate, an ongoing HBP can be continued without interruption or suspension, while the AV conduction status may be assessed. The atrial heart rate can be an atrial intrinsic rate (sinus rate, or AS rate), or an atrial pacing (AP) rate. The atrial heart rate can be determined using the P wave or atrial pacing artifacts sensed from an ECG or from an atrial EGM, or a far-field EGM (representing an electrical signature in the far field of atrium) using an electrode outside the atrium such as the proximal electrode 132. In some examples, the atrial heart rate includes a sensor-driven atrial pacing rate, determined based on patient physiologic response (e.g., physical activity or respiration). If atrial heart rate (e.g., AS, AP, or sensor-drive atrial pacing rate) exceeds a threshold (e.g., $HR_{block}$), then a presence of intermittent or rate-related AV conduction disturbance is indicated, and the present HBP therapy can be continued. However, if atrial heart rate slows down and falls below the threshold (e.g., $HR_{block}$), then an absence of intermittent or rate-related AV conduction disturbance is indicated, and the present HBP therapy can be discontinued.

Figure 5:
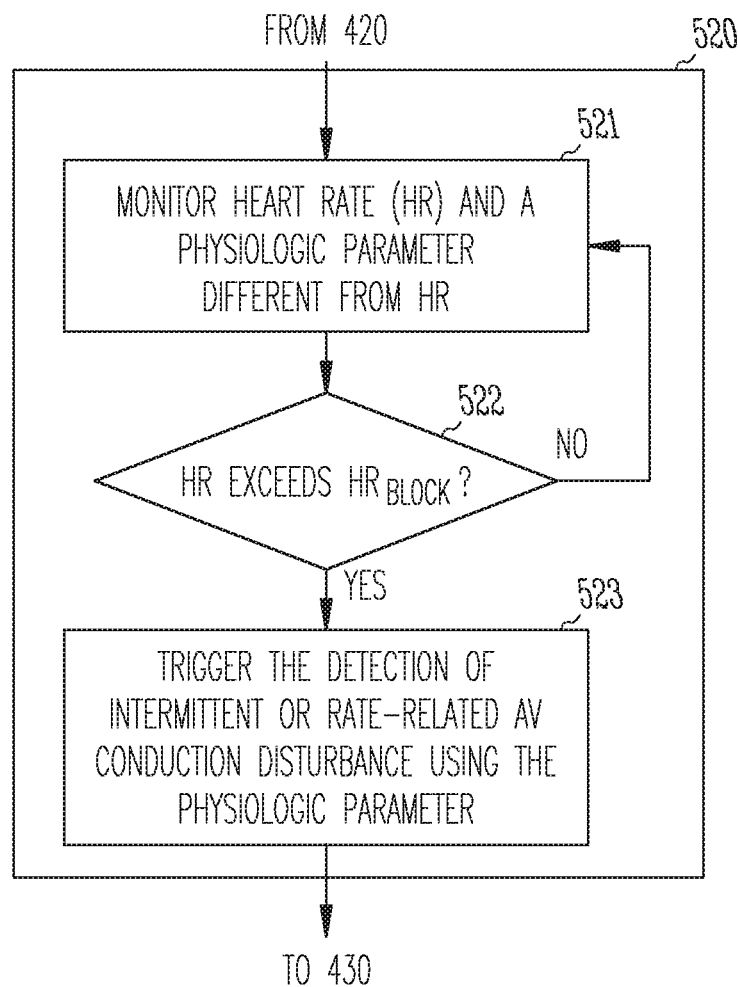
FIG. 5 is a flow chart illustrating an example of a method of sequentially detecting an indication of presence or absence of rate-related or intermittent AV conduction disturbance using heart rate and an additional physiologic parameter.

FIG. 5 is a flow chart illustrating an example of a method 520 of sequential detection an indication of presence or absence of rate-related or intermittent AV conduction disturbance using heart rate (HR) and at least one physiologic parameter different from the HR. The method 520 is an embodiment of a portion of the method 400, such as step 420. At 521, HR and at least one physiologic parameter different from HR, determined from the received physiologic information, may be monitored continuously or periodically (e.g., every 10 minutes). By way of example and not limitation, the physiologic parameter may include QRS width, AV interval, heart sounds, or cardiac timing, as illustrated in FIG. 3. At 522, the monitored HR can be compared to a heart rate threshold $HR_{block}$ (or a function of $HR_{block}$). If the monitored HR is below the $HR_{block}$, then the process goes back to 521 to continue monitoring the HR and the physiologic parameter. If the monitored HR exceeds the $HR_{block}$, then the detection of intermittent or rate-related AV conduction disturbance is initiated using the monitored physiologic parameter. Using HR exceeding the $HR_{block}$ to trigger the detection of intermittent or rate-related AV conduction disturbance can be performed using the control circuit 240. One or more of QRS width, AV interval, heart sounds, or cardiac timing, among other physiologic parameters, may be used to detect an intermittent or rate-related AV conduction disturbance using, are discussed above with reference to FIG. 3.

Figure 6:
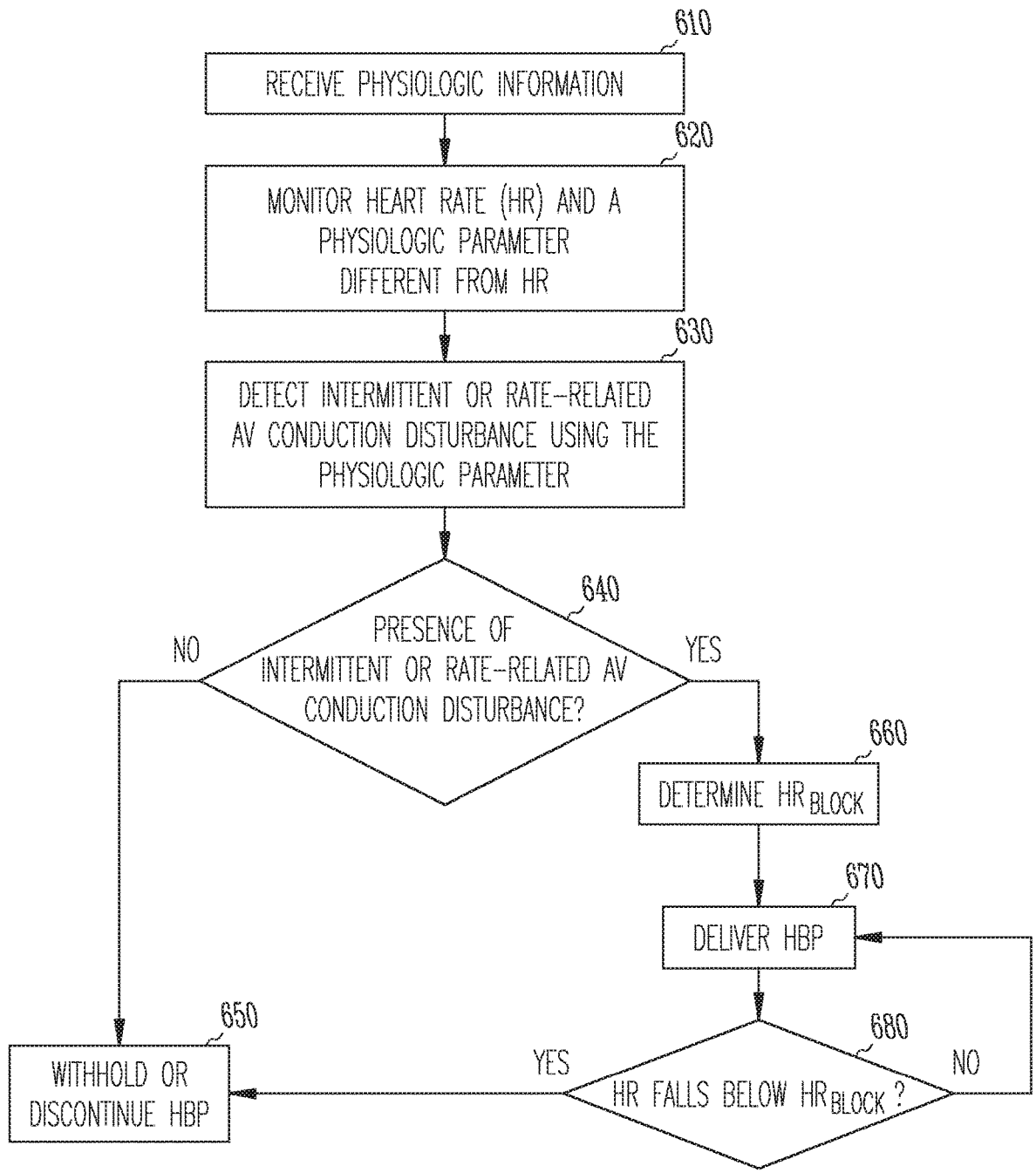
FIG. 6 is a flowchart illustrating another example of a method for providing HBP to correct rate-related or intermittent AV conduction abnormality.

FIG. 6 is a flowchart illustrating another example of a method 600 for providing His-bundle pacing (HBP) to correct rate-related or intermittent AV conduction abnormality in a patient using a medical-device system. The method 600 is an embodiment of the method 400, and can be implemented in, and executed by, the IMD 104, one or more devices in the external system 140, or the His-bundle pacing system 200. Similar to step 410, physiologic information may be received at 610. At 620, heart rate (HR) and at least one physiologic parameter different from the HR can be determined from the received physiologic information, and monitored continuously or periodically. By way of example and not limitation, the physiologic parameter can include QRS width, AV interval, heart sounds metrics, or cardiac timing, among other physiologic parameters, as illustrated in FIG. 3.

At 630, the physiologic parameter, other than the HR, can be used to generate an initial detection of intermittent or rate-related AV conduction disturbance, such as discussed above with reference to FIG. 3. HR may be monitored during the initial detection. A decision is made at 640 about presence or absence of an indication of the intermittent or rate-related AV conduction disturbance. If it is decided at 640 that no indication of intermittent or rate-related AV conduction disturbance is present, then at 650, the HBP may be withheld, or an ongoing HBP may be discontinued. If it is decided at 640 that an indication of intermittent or rate-related AV conduction disturbance is present, then at 660, a heart rate cutoff ($HR_{block}$) that corresponds to the initial detection of an event of intermittent or rate-related AV conduction disturbance can be determined. The $HR_{block}$ may be reported to a user (e.g., a clinician). Additionally or alternatively, the determined $HR_{block}$ may replace the existing heart rate threshold used in detecting rate-related or intermittent AV conduction disturbance. At 670, HBP may be delivered to the physiologic conduction pathway (e.g., His-bundle or a bundle branch). At 680, the monitored HR, optionally along with one or more physiologic parameter, may be used to determine whether the HBP needs to be continued or discontinued. In an example, the HBP can be continued without interruption, while the HR may be continuously scanned for resumption of normal conduction. If the patient HR exceeds the $HR_{block}$ determined at 660, then it is determined that the rate-related or intermittent AV conduction disturbance has not terminated, and the HBP can be continued at 670. If at 680 the patient HR falls below the $HR_{block}$, then it is determined that the rate-related or intermittent AV conduction disturbance has terminated, and the HBP can be discontinued at 650. When the HBP is discontinued, the pacing system may operate in a sense-only mode where no cardiac pacing is delivered. In some examples, at 680, resumption of normal conduction may be periodically searched (e.g., every 10 minutes). During the search period, the HBP can be temporarily suspended. Periodic searches may be used to detect paroxysmal AV block. If AV conduction disturbance persists, HBP can be resumed at 670 with appropriate AHI (e.g., approximately 50-120 msec) following an AS or an AP event. Otherwise, HBP can be discontinued at 650.

Figure 7:
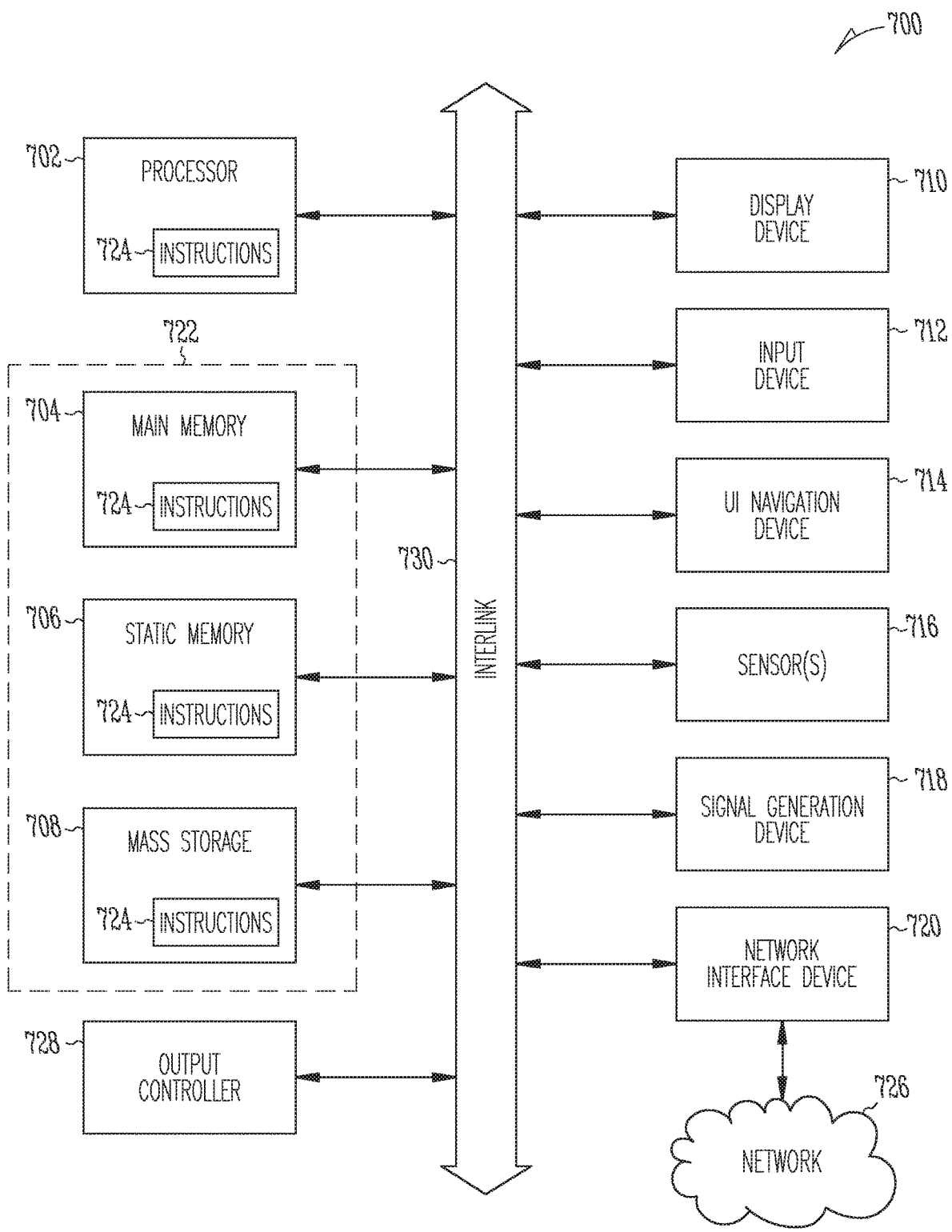
FIG. 7 illustrates a block diagram of an example machine upon which any one or more of the techniques (e.g., methodologies) discussed herein may perform.

FIG. 7 illustrates a block diagram of an example machine 700 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 700. Circuitry (e.g., processing circuitry) is a collection of circuits implemented in tangible entities of the machine 700 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 700 follow.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 700 may include a hardware processor 702 (e.g., a central processing unit (CPU), a graphics processing unit (GPU), a hardware processor core, or any combination thereof), a main memory 704, a static memory (e.g., memory or storage for firmware, microcode, a basic-input-output (BIOS), unified extensible firmware interface (UEFI), etc.) 706, and mass storage 708 (e.g., hard drive, tape drive, flash storage, or other block devices) some or all of which may communicate with each other via an interlink (e.g., bus) 730. The machine 700 may further include a display unit 710, an alphanumeric input device 712 (e.g., a keyboard), and a user interface (UI) navigation device 714 (e.g., a mouse). In an example, the display unit 710, input device 712, and UI navigation device 714 may be a touch screen display. The machine 700 may additionally include a signal generation device 718 (e.g., a speaker), a network interface device 720, and one or more sensors 716, such as a global positioning system (GPS) sensor, compass, accelerometer, or one or more other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 702, the main memory 704, the static memory 706, or the mass storage 708 may be, or include, a machine-readable medium 722 on which is stored one or more sets of data structures or instructions 724 (e.g., software) embodying or utilized by any one or more of the techniques or functions described herein. The instructions 724 may also reside, completely or at least partially, within any of registers of the processor 702, the main memory 704, the static memory 706, or the mass storage 708 during execution thereof by the machine 700. In an example, one or any combination of the hardware processor 702, the main memory 704, the static memory 706, or the mass storage 708 may constitute the machine-readable medium 722. While the machine-readable medium 722 is illustrated as a single medium, the term "machine-readable medium" may include a single medium or multiple media (e.g., a centralized or distributed database, and/or associated caches and servers) configured to store the one or more instructions 724.

The term "machine-readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may be further transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
an atrioventricular (AV) conduction monitor configured to:
receive physiologic information of a subject, the received physiologic information including a heart rate (HR);
determine for the subject, using the received physiologic information of the subject, a personalized HR threshold at and above which an intermittent or rate-related AV conduction disturbance occurs; and
detect an indication of either a presence or an absence of the intermittent or rate-related AV conduction disturbance in a heart of the subject using the received HR and the personalized HR threshold; and
a pacing control circuit configured to control an electrostimulation circuit to generate His-bundle pacing (HBP) pulses, and to provide a control signal to:
deliver HBP pulses to stimulate a physiologic conduction pathway of the heart in response to a detected indication of a presence of intermittent or rate-related AV conduction disturbance; and
withhold or discontinue delivery of the HBP pulses in response to a detected indication of an absence of intermittent or rate-related AV conduction disturbance.

2. The system of claim 1, wherein the AV conduction monitor is configured to:
determine the personalized HR threshold using intrinsic or paced AV conduction data of the subject; and
detect an indication of a presence of intermittent or rate-related AV conduction disturbance in response to the HR exceeding the personalized HR threshold, or an indication of an absence of intermittent or rate-related AV conduction disturbance in response to the HR is below the personalized HR threshold.

3. The system of claim 2, wherein the HR includes a sensed atrial heart rate.

4. The system of claim 3, wherein the HR includes an atrial pacing rate driven by a physiologic sensor.

5. The system of claim 2, wherein the AV conduction monitor is configured to monitor HR during the delivery of the HBP pulses, and the pacing control circuit is configured to provide a control signal to:
continue delivery of the HBP pulses in response to the indication of a presence of intermittent or rate-related AV conduction disturbance; and
discontinue delivery of the HBP pulses in response to the indication of an absence of intermittent or rate-related AV conduction disturbance.

6. The system of claim 1, wherein the AV conduction monitor is configured to:
determine a QRS width metric; and
detect an indication of a presence of intermittent AV conduction disturbance in response to the QRS width metric exceeding a QRS width threshold, or an indication of an absence of intermittent AV conduction disturbance in response to the QRS width metric falling below the QRS width threshold.

7. The system of claim 1, wherein the physiologic information includes cardiac acceleration information indicative of heart sounds (HS).

8. The system of claim 7, wherein the cardiac acceleration information includes an S1 heart sound intensity metric, and wherein the AV conduction monitor is configured to detect an indication of a presence of intermittent AV conduction disturbance in response to the S1 heart sound intensity metric falling below an S1 intensity threshold, or an indication of an absence of intermittent AV conduction disturbance in response to the S1 heart sound intensity metric exceeding the S1 intensity threshold.

9. The system of claim 1, wherein the physiologic includes a cardiac timing information.

10. The system of claim 9, wherein the cardiac timing information includes a pre-ejection period (PEP), and wherein the AV conduction monitor is configured to detect an indication of a presence of intermittent AV conduction disturbance in response to the PEP exceeding a PEP threshold, or an indication of an absence of intermittent AV conduction disturbance in response to the PEP falling below the PEP threshold.

11. The system of claim 1, wherein:
the AV conduction monitor is configured to monitor a physiologic parameter different from HR; and
the pacing control circuit is configured to, in response to the monitored HR exceeding the personalized HR threshold, trigger the AV conduction monitor to detect an indication of presence or absence of intermittent or rate-dependent AV conduction disturbance using the physiologic parameter.

12. The system of claim 1, wherein the AV conduction monitor is configured to:
monitor a physiologic parameter different from HR;
detect the indication of either a presence or an absence of an intermittent or rate-related AV conduction disturbance using the physiologic parameter; and
detect a HR corresponding to the detected indication of presence of intermittent or rate-related AV conduction disturbance; and
wherein the pacing control circuit is configured to provide a control signal to deliver, or withhold or discontinue, the HBP pulses using the detected HR corresponding to the detected indication of presence of intermittent or rate-related AV conduction disturbance.

13. The system of claim 12, comprising an output circuit configured to display the detected HR corresponding to the detected intermittent or rate-related AV conduction disturbance.

14. A method for pacing a physiologic conduction pathway including a His bundle or a bundle branch of a heart of a subject, the method comprising:
receiving physiologic information of the subject using an atrioventricular (AV) conduction monitor, the received physiologic information including a heart rate (HR);
determining for the subject, using the received physiologic information of the subject, a personalized HR threshold at and above which an intermittent or rate-related AV conduction disturbance occurs using the AV conduction monitor;

detecting, using the AV conduction monitor, an indication of either a presence or an absence of an intermittent or rate-related AV conduction disturbance in the heart of the subject using the received HR and the personalized HR threshold; and controlling, using a pacing control circuit, generation of His-bundle pacing (HBP) pulses of an electrostimulation circuit, comprising:

in response to an indication of a presence of intermittent or rate-related AV conduction disturbance, delivering HBP pulses to stimulate a physiologic conduction pathway; and in response to an indication of an absence of intermittent or rate-related AV conduction disturbance, withholding or discontinuing delivery of the HBP pulses.

15. The method of claim 14, wherein detecting an indication of either a presence or an absence of an intermittent or rate-related AV conduction disturbance includes:

determining the personalized HR threshold using intrinsic or paced AV conduction data of the subject; and detecting an indication of a presence of intermittent or rate-related AV conduction disturbance in response to the HR exceeding the personalized HR threshold, or an indication of an absence of intermittent or rate-related AV conduction disturbance in response to the HR is below the personalized HR threshold.

16. The method of claim 14, wherein detecting an indication of either a presence or an absence of an intermittent or rate-related AV conduction disturbance includes:

determining a QRS width metric; and detecting an indication of a presence of intermittent AV conduction disturbance in response to the QRS width metric exceeding a QRS width threshold, or an indication of an absence of intermittent AV conduction disturbance in response to the QRS width metric falling below the QRS width threshold.

17. The method of claim 14, wherein detecting an indication of either a presence or an absence of an intermittent or rate-related AV conduction disturbance includes:

determining an S1 heart sound intensity metric; and detecting an indication of a presence of intermittent AV conduction disturbance in response to the S1 heart sound intensity metric falling below an S1 intensity threshold, or an indication of an absence of intermittent AV conduction disturbance in response to the S1 heart sound intensity metric exceeding the S1 intensity threshold.

18. The method of claim 14, wherein detecting an indication of either a presence or an absence of an intermittent or rate-related AV conduction disturbance includes:

determining a pre-ejection period (PEP); and detecting an indication of a presence of intermittent AV conduction disturbance in response to the PEP exceeding a PEP threshold, or an indication of an absence of intermittent AV conduction disturbance in response to the PEP falling below the PEP threshold.

19. The method of claim 14, comprising:

monitoring a physiologic parameter different from HR; and in response to the monitored HR exceeding a HR threshold, triggering the detection of an indication of presence or absence of intermittent or rate-dependent AV conduction disturbance using the physiologic parameter.

20. The method of claim 14, comprising:

monitoring a physiologic parameter different from HR;

detecting the indication of either a presence or an absence of an intermittent or rate-related AV conduction disturbance using the physiologic parameter;

detecting a HR corresponding to the detected indication of presence of intermittent or rate-related AV conduction disturbance; and providing a control signal to deliver, or withhold or discontinue, the HBP pulses using the detected HR corresponding to the detected indication of presence of intermittent or rate-related AV conduction disturbance.

* * * * *